United States Patent [19]
Kluender et al.

[11] Patent Number: 5,939,583
[45] Date of Patent: Aug. 17, 1999

[54] SUBSTITUTED 4-BIPHENYL-4-HYDROXYBUTYRIC ACID DERIVATIVES AS MATRIX METALLOPROTEASE INHIBITORS

[75] Inventors: Harold C. E. Kluender, Trumbull; Susan M. Bjorge, Wallingford; Lisa Marie Zadjura, Old Saybrook; William Frederick Brubaker, Cheshire, all of Conn.

[73] Assignee: Bayer Corporation, Pittsburgh, Pa.

[21] Appl. No.: 08/960,921

[22] Filed: Oct. 30, 1997

Related U.S. Application Data

[60] Provisional application No. 60/030,264, Oct. 31, 1996.

[51] Int. Cl.[6] .......... A61K 31/405; A61K 31/40; C07D 207/08; C07D 209/48
[52] U.S. Cl. .......... 562/469; 514/417; 514/532; 514/543; 514/278; 548/479
[58] Field of Search .......... 548/479; 562/469; 514/278, 532, 543, 417

[56] References Cited

U.S. PATENT DOCUMENTS

| | | | |
|---|---|---|---|
| 3,462,483 | 8/1969 | Petrow et al. | 562/469 X |
| 4,021,479 | 5/1977 | Seeger et al. | 562/469 X |
| 4,151,302 | 4/1979 | Gante et al. | 424/317 |
| 4,168,385 | 9/1979 | Trust et al. | 560/56 |
| 4,304,931 | 12/1981 | Nicholson et al. | 562/469 |
| 4,562,263 | 12/1985 | Ohashi et al. | 548/479 |
| 4,567,289 | 1/1986 | Willard et al. | 560/59 |
| 4,855,321 | 8/1989 | Smith et al. | 514/532 |
| 5,001,128 | 3/1991 | Neuenschwander et al. | 514/278 |
| 5,393,780 | 2/1995 | Matsumoto et al. | 514/543 |

FOREIGN PATENT DOCUMENTS

| | | | |
|---|---|---|---|
| 60-169462 | 9/1985 | Japan | 548/479 |
| 9615096 | 5/1996 | WIPO . | |

OTHER PUBLICATIONS

Chem. Abstr. 120: 322938r (1994); Kuchar, Grimova, and Maturova, 4–(2,4–Difluorobiphenylyl)–4–hydroxy–2–methyl–butanoic acid and lactone, useful as antiinflammatories. Czech. CS 276, 834.

*Primary Examiner*—Floyd D. Higel

[57] ABSTRACT

Inhibitors for matrix metalloproteases, pharmaceutical compositions containing them, and a process for using them to treat a variety of physiological conditions. The compounds of the invention have the generalized formula

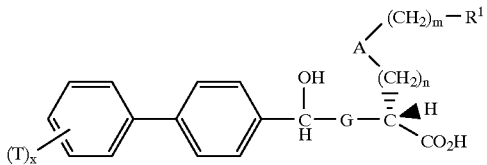

in which T is a pharmaceutically-acceptable substituent group; A is $CH_2$, CH, or N; G is $CH_2$ or CH; and $R^1$ is any of a variety of disclosed substituent groups. The class of compounds of the invention includes ring-containing materials in which the units A and G are joined. The compounds of the invention are mixtures of diastereomers, or individual diastereomers making up these mixtures.

16 Claims, No Drawings

SUBSTITUTED 4-BIPHENYL-4-HYDROXYBUTYRIC ACID DERIVATIVES AS MATRIX METALLOPROTEASE INHIBITORS

CROSS REFERENCE TO RELATED APPLICATIONS

This application is related to U.S. patent application Ser. No. 08/399,846, filed 15 Nov. 1994, now abandoned and to U.S. patent application Ser. No. 08/539,409, filed 6 Nov. 1995, now U.S. Pat. No. 5,789,434, and the corresponding PCT Application No. WO 9615096. The disclosures of U.S. patent applications having Ser. Nos. 08/399,846 and 08/539,409 are hereby incorporated by reference.

This application claims provisional of 60/030,264 filed Oct. 31, 1996.

FIELD

This invention relates to enzyme inhibitors, and more particularly, to novel 4-Biphenyl-4-hydroxybutyric Acid Derivatives useful for inhibiting matrix metalloproteases.

BACKGROUND

The matrix metalloproteases (also known as matrix metalloendo-proteinases or MMPs) are a family of zinc endoproteinases which include, but are not limited to, interstitial collagenase (also known as MMP-1), stromelysin (also known as proteoglycanase, transin, or MMP-3), gelatinase A (also known as 72kDa-gelatinase or MMP-2) and gelatinase B (also known as 95 kDa-gelatinase or MMP-9). These MMPs are secreted by a variety of cells including fibroblasts and chondrocytes, along with natural proteinatious inhibitors known as TIMPs (Tissue Inhibitor of MetalloProteinase).

All of these MMPs are capable of destroying a variety of connective tissue components of articular cartilage or basement membranes. Each MMP is secreted as an inactive proenzyme which must be cleaved in a subsequent step before it is able to exert its own proteolytic activity. In addition to the matrix destroying effect, certain of these MMPs such as MMP-3 have been implicated as the in vivo activator for other MMPs such as MMP-1 and MMP-9 (Ito, A. and Nagase, H., Arch. Biochem. Biophys., 26, 211–6 (1988); Ogata, Y.; Enghild, J. and Nagase, H., J. Biol. Chem. 267, 3581–4 (1992)). Thus, a cascade of proteolytic activity can be initiated by an excess of MMP-3. It follows that specific MMP-3 inhibitors should limit the activity of other MMPs that are not directly inhibited by such inhibitors.

It has also been reported that MMP-3 can cleave and thereby inactivate the endogenous inhibitors of other proteinases such as elastase (Winyard, P. G.; Zhang, Z.; Chidwick, K.; Blake, D. R.; Carrell, R. W.; Murphy, G., FEBS Lett. 279 91–4 (1991). Inhibitors of MMP-3 could thus influence the activity of other destructive proteinases by modifying the level of their endogenous inhibitors.

A number of diseases are thought to be mediated by excess or undesired matrix-destroying metalloprotease activity or by an imbalance in the ratio of the MMPs to the TIMPs. These include: a) osteoarthritis (Woessner, J. F., Jr.; Selzer, M. G., J. Biol. Chem. 259, 3633–8 (1984) and Phadke, K., J. Rheumatol. A, 852–60 (1983)), b) rheumatoid arthritis (Mullins, D. E.; Rohrlich, S. T., Biochim. Biophys. Acta 695 117–214 (1983); Woolley, D. E.; Crossley, M. J.; Evanson, M. J., Arthritis Rheum. 20, 1231–9 (1977); and Gravallese, E. M.; Darling, J. M.; Ladd, A. L.; Katz, J. N.; Glimcher, L. H., Arthritis Rheum. 3, 1076–84 (1991)), c) septic arthritis (Williams, R. J., III; Smith, R. L.; Schurman, D. J., Arthritis Rheum. 33, 533–41 (1990)), d) tumor metastasis (Reich, R.; Thompson, E. W.; Iwamoto, Y.; Martin, G. R.; Deason, J. R.; Fuller, G. C.; Miskin, R., Cancer Res. 48, 3307–12 (1988) and Matrisian, L. M.; Bowden, G. T.; Krieg, P.; Fuerstenberger, G.; Briand, J. P.; Leroy, P.; Breathnach, R., Proc. Natl. Acad. Sci. U.S.A. 83, 9413–7 (1986)), e) periodontal diseases (Overall, C. M.; Wiebkin, O. W.; Thonard, J. C. J. Peridontal. Res. 22, 81–8 (1987)), f) corneal ulceration (Burns, F. R.; Stack, M. S.; Gray, R. D.; Paterson, C. A., Invest. Ophthalmol. Vis. Sci. 30, 1569–75 (1989)), g) proteinuria (Baricos, W. H.; Murphy, G.; Zhou, Y.; Nguyen, H. H.; Shah, S. V., Biochem. J. 254, 609–12 (1988)), h) coronary thrombosis from atherosclerotic plaque rupture (Davies, M. J.; Foster, K.; Hembry, R.; Murphy, G.; Humphries, S., Proc. Natl. Acad. Sci. U.S.A. 88, 8154–8) (1991)), i) aneurysmal aortic disease (Vine, N.; Powell, J. T., Clin. Sci. 81, 233–9 (1991)), j) birth control (Woessner, J. F., Jr.; Morioka, N.; Zhu, C.; Mukaida, T.; Butler, T.; LeMaire, W. J., Steroids 54, 491–9 (1989)), k) dystrophobic epidermolysis bullosa (Kronberger, A.; Valle, K. J.; Eisen, A. Z.; Bauer, E. A., J. Invest. Dermatol. 79, 208–11 (1982)), and 1) degenerative cartilage loss following traumatic joint injury, conditions leading to inflammatory responses, osteopenias mediated by MMP activity, tempero mandibular joint disease, demyelating diseases of the nervous system, etc. (Chantry, A.; Earl, C.; Groome, N.; Glynn, P., J. Neurochem. 50, 688–94 (1988)).

The need for new therapies is especially important in the case of arthritic diseases. The primary disabling effect of osteoarthritis (OA), rheumatoid arthritis (AR) and septic arthritis is the progressive loss of articular cartilage and thereby normal joint function. No marketed pharmaceutical agent is able to prevent or slow this cartilage loss, although nonsteroidal antiinflammatory drugs (NSAIDs) have been given to control pain and swelling. The end result of these diseases is total loss of joint function which is only treatable by joint replacement surgery. MMP inhibitors are expected to halt or reverse the progression of cartilage loss and obviate or delay surgical intervention.

Proteases are critical elements at several stages in the progression of metastatic cancer. In this process, the proteolytic degradation of structural protein in the basal membrane allows for expansion of a tumor in the primary site, evasion from this site as well as homing and invasion in distant, secondary sites. Also, tumor induced angiogenesis is required for tumor growth and is dependent on proteolytic tissue remodeling. Transfection experiment with various types of proteases have shown that the matrix metalloproteases, in particular, gelatinases A and B (MMP-2 and MMP-9, respectively) play a dominant role in these processes. For an overivew of this field see Mullins, D. E.; Rohrlich, S. T., Biochim. Biophys. Acta 695, 177–214 (1983); Ray, J. M.; Stetler-Stevenson, W. G., Eur. Respir. J. 7, 2062–72 (1994) and Birkedal-Hansen, H.; Moore, W. G. I.; Bodden, M. K.; Windsor, L. J.; Birkedal-Hansen, B.; DeCarlo, A.; Englar, J. A., Crit. Rev. Oral. Biol. Med. 4, 197–250 (1993).

Furthermore, it could be shown that inhibition of degradation of extracellular matrix by the native matrix metalloprotease inhibitor TIMP-2 (a protein) arrests cancer growth (De Clerck, Y. A.; Perez, N.; Shimada, H.; Boone, T. C.; Langley, K. E.; Taylor, S. M., Cancer Res. 52, 701–8 (1992)) and that TIMP-2 inhibits tumor-induced angiogenesis in experimental systems (Moses, M. A.; Sudhalter, J.; Langer, R., Science 248, 1408–10 (1990)). For a review see De Clerck, Y.; Shimada, H.; Taylor, S. M.; Langley, K. E., Ann.

N. Y. Acad. Sci. 732, 222–32 (1994). It was also demonstrated that the synthetic matrix metalloprotease inhibitor batimastat when given intraperitoneally inhibits human colon tumor growth and spread in an orthotopic model in nude mice (Wang, X.; Fu, X.; Brown, P. D.; Crimmin, M. J.; Hoffman, R. M. Cancer Res. 54, 4726–8 (1994)) and prolongs the survival of mice bearing human ovarian carcinoma xenografts (Davies, B.; Brown, P. D.; East, N.; Crimmin, M. J.; Balkwill, F. R., Cancer Res. 53, 2087–91 (1993)). The use of this and related compounds has been described in WO-A-9321942.

There are several patents and patent applications disclosing the use of metalloproteinase inhibitors for the retardation of metastatic cancer, promoting tumor regression, inhibiting cancer cell proliferation, slowing or preventing of cartilage loss associated with osteoarthritis or for treatment of other diseases as indicated above (e.g. WO-A-9519965; WO-A-9519956; WO-A-9519957; WO-A-9519961; WO-A-9321942; WO-A-9321942; WO-9421625; U.S. Pat. No. 4,599,361; U.S. Pat. No. 5,190,937; EP 0574 758 A1, published Dec. 22, 1993; EP 026 436 A1 published Aug. 3, 1988; and EP 0520 573 A1, published Dec. 30, 1992). The preferred compounds of these patents have peptide backbones with a zinc complexing group (hydroxamic acid, thiol, carboxylic acid or phosphinic acid) at one end and a variety of side chains, both those found in the natural amino acids as well as those with more novel functional groups. Such small peptides are often poorly absorbed, exhibiting low oral bioavailability. They are also subject to rapid proteolytic metabolism, thus having short half lives. As an example, batimastat, the compound described in WO-A-9321942, can only be given intraperitoneally.

WO 9615096, published 23 May, 1996 describes substituted 4-biarylbutyric or 5-biarylpentanoic acids and derivatives as matrix metalloprotease inhibitors. This is a continuation-in-part of U.S. application Ser. No. 08/339,846, filed Nov. 15, 1994, which was incorporated by reference. The application discloses two substituted 4-biphenyl-4-hydroxybutyric acid derivatives (examples 33 and 34, shown below). These compounds are less potent as MMP-3 inhibitors than the corresponding 4-biphenyl-4-oxobutyric acid derivatives.

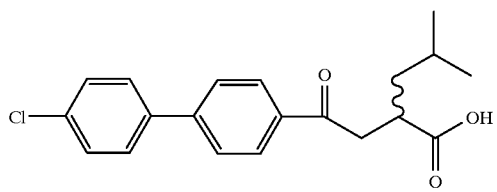

WO 9615096 Example 1
$IC_{50}$ 486 nM (vs. MMP-3)

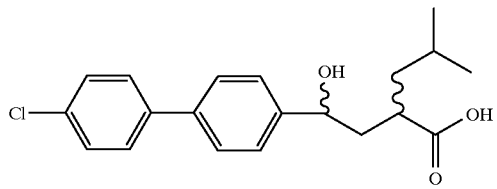

Isomer A WO 9615096 Example 33
$IC_{50}$ 2,600 nM (vs. MMP-3)

Isomer B WO 9615096 Example 34
$IC_{50}$ 5,000 nM (vs. MMP-3)

It is desirable to have effective MMP inhibitors which possess improved bioavailabilty and biological stability relative to the peptide-based compounds of the prior art, and which can be optimized for use against particular target MMPs. Such compounds are the subject of the present application.

SUMMARY

In view of the fact that the substituted 4-biaryl-4-hydroxybutyric acids disclosed in WO 9615096 appear to be less active as MMP inhibitors than the analogous identically substituted 4-biaryl-4-oxobutyric acid, it is suprising that it has now been found that the active isomer of other 4-biaryl-4-hydroxybutyric acids may be significantly more potent as MMP inhibitors than the corresponding 4-oxo compounds.

The present invention relates to compounds having matrix metalloprotease inhibitory activity and the general formula (I) below

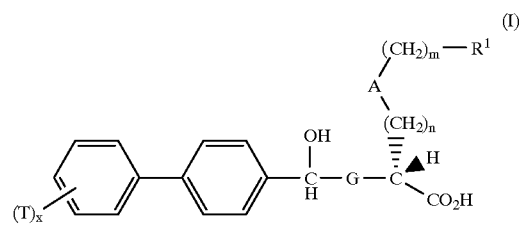

wherein:
T is a pharmaceutically-acceptable substituent group;
x is 0, 1, or 2;
m is 0 or an integer of 1–4;
n is 0 or 1; and
either
A and G are both $CH_2$; or
A is a chemical bond and G is $CH_2$; or
A is CH or N; and
G is CH; and
A is connected to G by a ring-forming linkage of formula:
$(CH_2)_{0-3}(Q)(CH_2)_{0-3}$ ; wherein
Q is a chemical bond, S, or O; and
C, S, and O constitute linking atoms;
resulting in formation of a ring which includes A, said ring-forming linkage, and G;
with the provisos that
the sum of n plus the total number of linking atoms in said ring-forming linkage is an integer of from 1 to 4; and the number of heteroatoms in said ring is 0 or 1;
$R^1$ is:
aryl of 6–10 carbons, provided that if this aryl group is phenyl, then x is 1 or 2;
heteroaryl comprising 4–9 carbons and at least one N, O, or S heteroatom;
aryl-substituted alkenyl wherein the aryl portion contains 6–10 carbons and the alkenyl portion contains 2–5 carbons;
hetaryl-substituted alkenyl wherein the heteroaryl portion comprises 4–9 carbons and at least one N, O, or S heteroatom, and the alkenyl portion contains 2–5 carbons;
aryl-substituted alkynyl wherein the aryl portion contains 6–10 carbons and the alkynyl portion contains 2–5 carbons;
heteroaryl-substituted alkynyl wherein the heteroaryl portion comprises 4–9 carbons and at least one N, O, or S heteroarom and the alkynyl portion contains 2–5 carbons;
N-phthalimidoyl;
N-(1,2-naphthalenedicarboximidoyl);
N-(2,3-naphthalenedicarboximidoyl);

N-(1,8-naphthalenedicarboximidoyl);
N-indoloyl;
N-(2-pyrrolodinonyl);
N-succiniimidoyl;
N-maleimidoyl;
3-hydantoinyl;
1,2,4-urazolyl;
amido;
a urethane;
a urea;

wherein Y is O or S, $R^2$ is H or alkyl of 1–3 carbon atoms and u is 0, 1, or 2
an amino; and
$ZR^8$ in which
Z represents

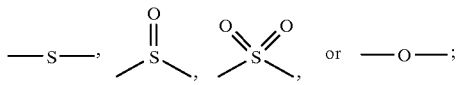

$R^8$ is:
  aryl of 6–10 carbons;
  heteroaryl comprising 4–9 carbons and at least one N, O, or S heteroatom;
  arylalkyl wherein the aryl portion contains 6–12 carbons and the alkyl portion contains 1–4 carbons; or
  heteroaryl-alkyl wherein the aryl portion comprises 4–9 carbons and at least one N, O, or S heteroatom and the alkyl portion contains 1–4 carbons;
and with the proviso that
  when Z is O, $R^8$ may also be alkyleneoxy or polyalkyleneoxy terminated with H, alkyl, or phenyl.

Aryl or heteroaryl portions of any of the T or $R^1$ groups optionally may bear up to two substituents which are selected from the group consisting of $-(CH_2)_yC(R^{11})(R^{12})OH$, $-(CH_2)_yOR^{11}$, $-(CH_2)_ySR^{11}$, $-(CH_2)_yS(O)R^{11}$, $-(CH_2)_yS(O)_2R^{11}$, $-(CH_2)_ySO_2N(R^{11})_2$, $-(CH_2)_yN(R^{11})_2$, $-(CH_2)_yN(R^{11})COR^{12}$, $-OC(R^{11})_2O-$ in which both oxygen atoms are connected to the aryl ring, $-(CH_2)_yCOR^{11}$, $-(CH_2)_yCON(R^{11})_2$, $-(CH_2)_yCO_2R^{11}$, $-(CH_2)_yOCOR^{11}$, -halogen, $-CHO$, $-CF_3$, $-NO_2$, $-CN$, and $-R^{12}$, in which y is 0–4; $R^{11}$ represents H or lower alkyl of 1–4 carbon atoms; and $R^{12}$ represents lower alkyl of 1–4 carbon atoms.

As prepared, the compounds of the invention are mixtures of diastereomers. For each compound, the materials of interest are the mixtures of diastereomers or the single diastereomer which has the greater MMP inhibitory activity of the diastereomers constituting the mixture of diastereomers. Pharmaceutically acceptable salts are also within the scope of the invention.

In addition to the above-described compounds, the invention also relates to pharmaceutical compositions comprising a compound of the invention as described above and in more detail in the detailed description below, plus a pharmaceutically acceptable carrier.

The invention further relates to a method for treating a matrix metalloprotease-mediated condition in a mammal to achieve an effect, comprising administering to the mammal an amount of a compound of the invention as described above and in more detail in the detailed description below, which is effective to treat the condition.

DETAILED DESCRIPTION

This invention pertains broadly to matrix metalloprotease-inhibiting compounds having general formula (I), shown above.

The symbol "T" in formula (I) stands for a pharmaceutically-acceptable substituent group. Exemplary groups "T" are moieties such as halogen; alkyl; haloalkyl; alkenyl; alkynyl; $-(CH_2)_pQ$ in which p is 0 or an integer of 1–4; and -alkenyl-Q in which the alkenyl moiety comprises 2–4 carbons. Q in the latter two groups may be aryl, heteroaryl, $-CN$, $-CHO$, $-NO_2$, $-CO_2R^4$, $-OCOR^4$, $-SOR^5$, $-SO_2R^5$, $-CON(R^4)_2$, $-SO_2N(R^4)_2$, $-COR^4$, $-N(R^4)_2$, $-N(R^4)COR^4$, $-N(R^4)CO_2R^5$, $-N(R^4)CON(R^4)_2$, $-OR^6$, and $-SR^6$. In these formulae $R^4$ represents H, alkyl, aryl, heteroaryl, arylalkyl, or heteroaryl-alkyl; $R^5$ represents alkyl, aryl, heteroaryl, arylalkyl, or heteroaryl-alkyl; and $R^6$ represents H, alkyl, aryl, heteroaryl, arylalkyl, heteroaryl-alkyl, alkenyl, alkynyl, haloalkyl, acyl, or alkyleneoxy or polyalkyleneoxy terminated with H, alkyl, or phenyl. Unsaturation in a moiety which is encompassed by Q or which is part of Q is separated from any N, O, or S of Q by at least one carbon atom. The terminating phenyl ring of (I) may be unsubstituted or may carry up to 2 substituents T. Accordingly, the subscript x is 0, 1, or 2.

In the text immediately above dealing with "T", the following further definitions apply: "alkyl" means straight, branched, cyclic and polycyclic hydrocarbon groups containing 1–10 carbon atoms; "haloalkyl" means partially or fully halogenated alkyl groups containing 1–10 carbons; "alkenyl" means straight, branched, cyclic and polycyclic unsaturated hydrocarbon groups containing 2–10 carbons and at least one double bond; "alkynyl" means straight, branched, cyclic and polycyclic hydrocarbon groups containing 2–10 carbons and at least one triple bond; "aryl" means aromatic carbocycle of carbobicycle group of 6–12 carbons such as phenyl, biphenyl, or naphthyl; "heteroaryl" means aromatic cyclic groups of 6–12 atoms containing 1–4 heteroatoms selected from O, N, and S; "arylalkyl" means an alkyl chain of 1–4 carbons terminated with an aryl group; "heteroaryl-alkyl" means an alkyl chain of 1–4 carbons terminated with a heteroaryl group; "acyl" means $-$COalkyl, Coaryl, or COheteroaryl; "alkyleneoxy" means a diradical chain of 1–6 methylenes and 1 oxygen; and "polyalkyleneoxy" means a diradical chain of 1–6 methylenes and 2–3 oxygens, with the proviso that each oxygen is separated from each other oxygen by at least one carbon.

More particularly, the invention relates in a first aspect to compounds of formula (I) in which each of A and G is $CH_2$, and n is 0. Such compounds have the formula (II) shown below.

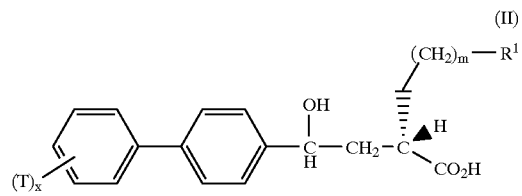

In formula (II), m is preferably 0, 1, or 2. Further, when m is 0, $R^1$ is preferably

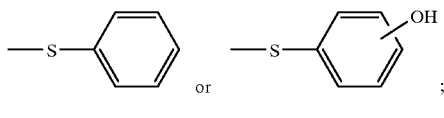

when m is 1, $R^1$ is preferably

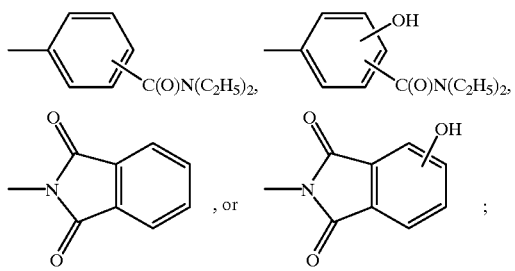

when m is 2, $R^1$ is preferably

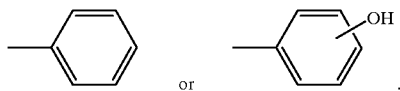

In a more preferred aspect, in formula (II) T is halogen or $OR^6$ wherein $R^6$ is alkyl of 1–6 carbons or benzyl; x is 1; m is 0 or 2; and when m is 0, $R^1$ is

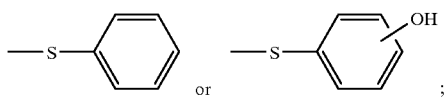

and when m is 2, $R^1$ is

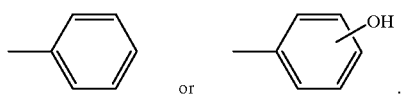

In addition to compounds of formula (II), the invention relates in a second aspect to compounds of formula (I) in which n is 0 or 1; A is CH or N; G is CH; and A is connected to G by a ring-forming linkage of formula $(CH_2)_{0-3}(Q)(CH_2)_{0-3}$ in which Q is a chemical bond, S, or O; and C, S, and O constitute linking atoms. These parameter selections result in formation of a ring which includes A, the above-described ring-forming linkage, and G. This subset of compounds is based on formula (I) with the provisos that the sum of n plus the total number of linking atoms in the ring-forming linkage is an integer of from 1 to 4; and the number of heteroatoms in the ring is 0 or 1. T, x, m, and $R^1$ are as defined in connection with formula (I). These compounds thus possess a 4- to 7-membered ring which may include a heteroatom of N, O, or S, and are represented by formula (III) below.

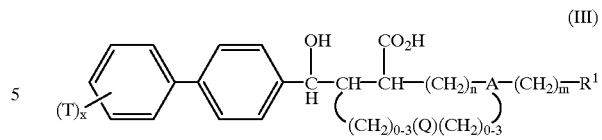

In a preferred subset of the above-described ring-containing compounds, n is 0; A is CH; Q is a chemical bond; and the ring-forming linkage is $-(CH_2)_2-$. The resulting compounds have the formula (IIIa) shown below.

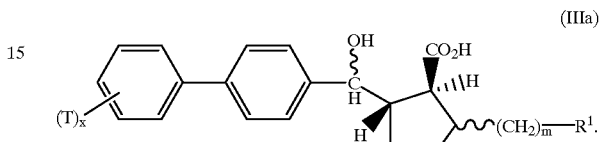

Most preferably, the compounds of formula (IIIa) are materials in which T is halogen or $OR^6$ in which $R^6$ is alkyl of 1–6 carbons or benzyl; x is 1; and m is 0 or 1. When m is 0, $R^1$ is most preferably

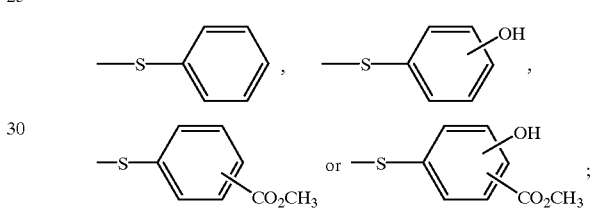

and when m is 1, $R^1$ is most preferably

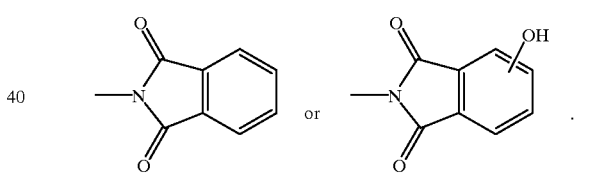

Those skilled in the art will appreciate that each of the compounds of the invention exists in more than one diastereomeric form, and understand that such stereoisomers generally exhibit different activities in biological systems. This invention encompasses all possible stereoisomers which possess inhibitory activity against an MMP, regardless of their stereoisomeric designations, although only the more active of the strereoisomers in each mixture has been claimed herein. It also encompasses mixtures of stereoisomers in which at least one member possesses MMP inhibitory activity.

The invention also encompasses pharmaceutically acceptable "prodrugs" of the claimed compounds. These are typically acylated derivatives of alcohol-containing compounds of the invention, or lower alkyl esters and lower alkyl amides of the carboxylic acid moiety, as well as lactones formed by reaction between the carboxylic acid function and the hydroxyl group. Other types of prodrugs are known, however. Such prodrugs, which may be intrinsically physiologically inactive or active, are converted to the active compounds of the invention in the body of the treated subject. A schematic of the interconversion of the lactone and straight chain forms of a material is shown below.

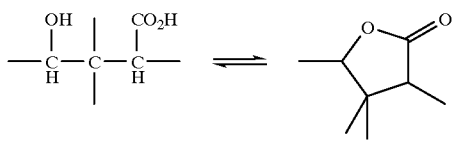

Preparation of such derivatives is within the skill of the art.

The most preferred compounds of the present invention are as indicated and named in the list below.

4-[4-(4-chlorophenyl)phenyl]-4-hydroxy-2-(phenylthiomethyl)butanoic acid;

[2S, 4R]-4-[4-(4-chlorophenyl)phenyl]-4-hydroxy-2-(phenylthiomethyl)-butanoic acid;

4-[4-(4-chlorophenyl)phenyl]-4-hydroxy-2-[(4-hydroxyphenyl)-thiomethyl]-butanoic acid;

the more active of the compounds [2S, 4R]-4-[4-(4-chlorophenyl)phenyl]-4-hydroxy-2-[(4-hydroxyphenyl)-thiomethyl]butanoic and [2S, 4S]-4-[4-(4-chlorophenyl)phenyl]-4-hydroxy-2-[(4-hydroxyphenyl)-thiomethyl]butanoic acid;

4-[4-(4-chlorophenyl)phenyl]-4-hydroxy-2-(3-phenylpropyl)butanoic acid;

the more active of the compounds [2S, 4R]-4-[4-(4-chlorophenyl)phenyl]-4-hydroxy-2-(3-phenylpropyl)-butanoic acid and [2S, 4S]-4-[4-(4-chlorophenyl)phenyl]-4-hydroxy-2-(3-phenylpropyl)-butanoic acid;

4-[4-(4-chlorophenyl)phenyl]-4-hydroxy-2-[2-(3-N,N-diethylcarbamoyl)-phenylethyl]butanoic acid the more active of the compounds [2S, 4R]-4-[4-(4-chlorophenyl)phenyl]-4-hydroxy-2-[2-(3-N,N-diethylcarbamoyl)phenylethyl]butanoic acid and [2S, 4S]-4-[4-(4-chlorophenyl)phenyl]-4-hydroxy-2-[2-(3-N,N-diethylcarbamoyl)phenylethyl]butanoic acid;

4-[4-(4-pentyloxyphenyl)phenyl]-4-hydroxy-2-(3-phenylpropyl)butanoic acid the more active of the compounds [2S, 4R]-4-[4-(4-pentyloxyphenyl)phenyl]-4-hydroxy-2-(3-phenylpropyl)-butanoic acid and [2S, 4S]-4-[4-(4-pentyloxyphenyl)phenyl]-4-hydroxy-2-(3-phenylpropyl)-butanoic acid;

4-[4-(4-benzyloxyphenyl)phenyl]-4-hydroxy-2-(3-phenylpropyl)butanoic acid the more active of the compounds [2S, 4R]-4-[4-(4-benzyloxyphenyl)phenyl]-4-hydroxy-2-(3-phenylpropyl)-butanoic and [2S, 4S]-4-[4-(4-benzyloxyphenyl)phenyl]-4-hydroxy-2-(3-phenylpropyl)-butanoic acid;

4-[4-(4-chlorophenyl)phenyl]-4-hydroxy-2-(2-phthalimidoethyl)butanoic acid the more active of the compounds [2S, 4R]-4-[4-(4-chlorophenyl)phenyl]-4-hydroxy-2-(2-phthalimidoethyl)-butanoic acid and [2S, 4S]-4-[4-(4-chlorophenyl)phenyl]-4-hydroxy-2-(2-phthalimidoethyl)-butanoic acid;

trans-5-[(4-(4-chlorophenyl)phenyl)hydroxymethyl]-trans-2-phenylthio-cyclopentanecarboxylic acid;

the more active of the compounds (1S,2R,5S)-trans-5-[(4-(4-chlorophenyl)phenyl)-S-hydroxymethyl]-trans-2-phenylthiocyclopentanecarboxylic acid; and (1S,2R,5S)-trans-5-[(4-(4-chlorophenyl)phenyl)-R-hydroxymethyl]-trans-2-phenylthiocyclopentanecarboxylic acid;

trans-5-[(4-(4-chlorophenyl)phenyl)hydroxymethyl]-cis-2-(2-methoxy-carbonyl-phenylthio)cyclopentanecarboxylic acid the more active of the compounds (1S,2S,5S)-trans-5-[(4-(4-chlorophenyl)phenyl)-S-hydroxymethyl]-cis-2-(2-methoxycarbonylphenylthio)cyclopentanecarboxylic acid and (1S,2S,5S)-trans-5-[(4-( 4-chlorophenyl)phenyl)-R-hydroxymethyl]-cis-2-(2-methoxycarbonylphenylthio)cyclopentanecarboxylic acid;

trans-5-[(4-(4-chlorophenyl)phenyl)hydroxymethyl]-trans-2-phthalimido-methylcyclopentanecarboxylic acid; and the more active of the compounds (1S,2R,5S)-trans-5-[(4-(4-chlorophenyl)phenyl)-S-hydroxymethyl]-trans-2-phthalimidomethylcyclopentanecarboxylic acid and (1S,2R,5S)-trans-5-[(4-(4-chlorophenyl)phenyl)-R-hydroxymethyl]-trans-2-phthalimidomethylcyclopentanecarboxylic acid.

General Preparative Methods

The compounds of the invention may be prepared readily by use of known chemical reactions and procedures. Nevertheless, the following general preparative methods are presented to aid the reader in synthesizing the inhibitors, with more detailed examples being presented below in the experimental section.

All variable groups of these methods are as described in the generic description if they are not specifically defined below.

General Method A

The compounds of this invention are conveniently prepared by reduction of substituted 4-biphenyl-4-oxobutyric acid derivatives with a selective hydride reducing agent such as sodium borohydride or sodium cyanoborohydride in a solvent such as ethanol or tetrahydrofuran at 0° C. to ambient temperature. Alternatively, the reducing agent can be any number of other reagents used by one skilled in the art to reduce a carbonyl to a secondary alcohol, with the provise that such reducing agent does not effect undesired changes in the T, carboxy, or $R^1$ parts of such starting materials.

The isomers of the product can be isolated in pure form by a combination of crystallization and chromatography. The starting 4-biphenyl-4-oxobutyric acid derivatives are prepared as described in U.S. application Ser. No. 08/539,409 and WO9615096.

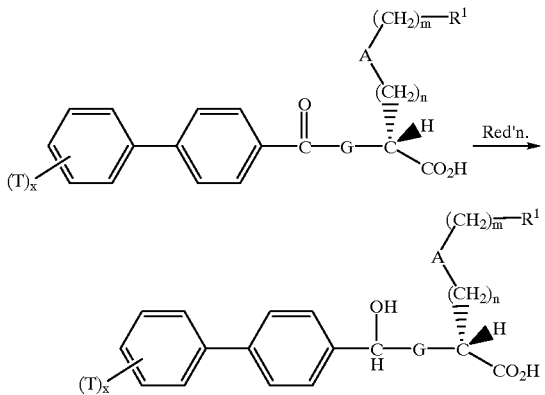

General Method B—Isomerically pure materials are conveniently prepared as in Method A but by using a chiral reducing agent such as the CBS system (Corey, E. J.; Bakshi, R. K.; Shibata, S., *J. Am. Chem. Soc.* 1987, 109, 5551–5553, or Corey, E. J.; Bakshi, R. K.; Shibata, S.; Chen, C. -P.; Singh, V. K., *J. Am. Chem. Soc.* 1987, 109, 7925–7926.) instead of sodium borohydride.

Suitable pharmaceutically acceptable salts of the compounds of the present invention include addition salts formed with organic or inorganic bases. The salt forming ion derived from such bases can be metal ions, e.g., aluminum, alkali metal ions, such as sodium of potassium, alkaline earth metal ions such as calcium or magnesium, or an amine salt ion, of which a number are known for this purpose. Examples include ammonium salts, arylalkylamines such as dibenzylamine and N,N-dibenzylethylenediamine, lower alkylamines such as methylamine, t-butylamine, procaine, lower alkylpiperidines such as N-ethylpiperidine, cycloalkylamines such as cyclohexylamine or dicyclohexylamine, 1-adamantylamine, benzathine, or salts derived from amino acids like arginine, lysine or the like. The physiologically acceptable salts such as the sodium or potassium salts and the amino acid salts can be used medicinally as described below and are preferred.

These and other salts which are not necessarily physiologically acceptable are useful in isolating or purifying a product acceptable for the purposes described below. For example, the use of commercially available enantiomerically pure amines such as (+)-cinchonine in suitable solvents can yield salt crystals of a single enantiomer of the invention compounds, leaving the opposite enantiomer in solution in a process often referred to as "classical resolution." As one enantiomer of a given invention compound is usually substantially greater in physiological effect than its antipode, this active isomer can thus be found purified in either the crystals or the liquid phase. The salts are produced by reacting the acid form of the compound with an equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc.

Suitable ester and amide derivatives of the compounds of the invention are, for example, alkyl and aryl carboxylic acid esters of the 4-hydroxyl group or alkyl or aryl esters of the carboxylic acid, or amides prepared from the carboxylic adid together with lower alkyl amines or matural amino acids.

The compounds of the present invention have been found to inhibit the matrix metalloproteases MMP-3, MMP-9, and MMP-2, and are therefore useful for treating or preventing the conditions referred to above. As other MMPs not listed above share a high degree of homology with those listed above, especially in the catalytic site, it is deemed that compounds of the invention should also inhibit such other MMPs to varying degrees. Varying the substituents on the aryl portions of the molecules, as well as those of the butanoic acid chain of the claimed compounds, has been demonstrated to affect the relative inhibition of the listed MMPs. Thus compounds of this general class can be "tuned" by selecting specific substituents such that inhibition of specific M(s) associated with specific pathological conditions can be enhanced while leaving non-involved MMPs less affected.

The inhibitors of the present invention are contemplated for use in human and veterinary applications. Accordingly, this invention relates to a method for treating mammalian subjects (including humans and/or animals raised in the dairy, meat, or fur industries or as pets, for example, mice, rats, horses, cattle, sheep, dogs, cats, etc.) suffering from matrix metalloprotease-mediated conditions such as those previously described, by administering an effective amount of a compound of the invention. In this treatment method the mammal is preferably a human. The effects which can be achieved are: alleviation of osteoarthritis, rheumatoid arthritis, septic arthritis, periodontal disease, corneal ulceration, proteinuria, aneurysmal aortic disease, dystrophobic epidermolysis bullosa, conditions leading to inflammatory responses, osteopenias mediated by MMP activity, tempero mandibular joint disease, or demyelating diseases of the nervous system; retardation of tumor metastasis or degenerative cartilage loss following traumatic joint injury; reduction of coronary thrombosis from atherosclerotic plaque rupture; or improved birth control. In this treatment method the amount of the inhibitor compound is effective to inhibit the activity of at least one matrix metalloprotease, resulting in achievement of the desired effect.

The compounds of the invention are employed in pharmaceutical compositions containing active ingredient(s) plus one or more pharmaceutically acceptable carriers, diluents, fillers, binders, and other excipients, depending on the administration mode and dosage form contemplated.

Administration of the inhibitors may be by any suitable mode known to those skilled in the art. Examples of suitable parenteral administration include intravenous, intraarticular, subcutaneous and intramuscular routes.

Intravenous administration can be used to obtain acute regulation of peak plasma concentrations of the drug. Improved half-life and targeting of the drug to the joint cavities may be aided by entrapment of the drug in liposomes. It may be possible to improve the selectivity of liposomal targeting to the joint cavities by incorporation of ligands into the outside of the liposomes that bind to synovial-specific macromolecules. Alternatively intramuscular, intraarticular or subcutaneous depot injection with or without encapsulation of the drug into degradable microspheres e.g., comprising poly(DL-lactide-co-glycolide) may be used to obtain prolonged sustained drug release. For improved convenience of the dosage form it may be possible to use an i.p. implanted reservoir and septum such as the Percuseal system available from Pharmacia. Improved convenience and patient compliance may also be achieved by the use of either injector pens (e.g. the Novo Pin or Q-pen) or needle-free jet injectors (e.g. from Bioject, Mediject or Becton Dickinson). Prolonged zero-order or other precisely controlled release such as pulsatile release can also be achieved as needed using implantable pumps with delivery of the drug through a cannula into the synovial spaces. Examples include the subcutaneously implanted osmotic pumps available from ALZA, such as the ALZET osmotic pump.

Nasal delivery may be achieved by incorporation of the drug into bioadhesive particulate carriers (<200 $\mu$m) such as those comprising cellulose, polyacrylate or polycarbophil, in conjunction with suitable absorption enhancers such as phospholipids or acylcamitines. Available systems include those developed by DanBiosys and Scios Nova.

Oral delivery may be achieved by incorporation of the drug into tablets, coated tablets, dragées, hard and soft gelatin capsules, solutions, emulsions or suspensions. Oral delivery may also be achieved by incorporation of the drug into enteric coated capsules designed to release the drug into the colon where digestive protease activity is low. Examples include the OROS-CT/Osmet™ and PULSINCAP™ systems from ALZA and Scherer Drug Delivery Systems respectively. Other systems use azo-crosslinked polymers that are degraded by colon specific bacterial azoreductases, or pH sensitive polyacrylate polymers that are activated by the rise in pH at the colon. The above systems may be used in conjunction with a wide range of available absorption enhancers.

Rectal delivery may be achieved by incorporation of the drug into suppositories.

The compounds of this invention can be manufactured into the above listed formulations by the addition of various therapeutically inert, inorganic or organic carriers well known to those skilled in the art. Examples of these include, but are not limited to, lactose, corn starch or derivatives thereof, talc, vegetable oils, waxes, fats, polyols such as polyethylene glycol, water, saccharose, alcohols, glycerin and the like. Various preservatives, emulsifiers, dispersants, flavorants, wetting agents, antioxidants, sweeteners, colorants, stabilizers, salts, buffers and the like are also added, as required to assist in the stabilization of the formulation or to assist in increasing bioavailability of the active ingredient(s) or to yield a formulation of acceptable flavor or odor in the case of oral dosing.

The amount of the pharmaceutical composition to be employed will depend on the recipient and the condition being treated. The requisite amount may be determined without undue experimentation by protocols known to those skilled in the art. Alternatively, the requisite amount may be calculated, based on a determination of the amount of target enzyme which must be inhibited in order to treat the condition. Typically, dosage levels from about 0.05 mg to about 150 mg per kilogram of body weight per day (about 4 mg to about 12 grams per adult human subject per day) are useful in the treatment of the above-indicated conditions. It is to be understood, however, that the specific dose level for any particular subject will depend upon a variety of factors including the subject's age, body weight, general health, sex, and diet, the activity and expected level of side effects of the specific compound employed, the time and route of administration, the rate of excretion, as well as drug combinations and the severity of the particular condition being treated.

The matrix metalloprotease inhibitors of the invention are useful not only for treatment of the physiological conditions discussed above, but are also useful in such activities as purification of metalloproteases, and in testing for matrix metalloprotease activity. Such activity testing can be both in vitro using natural or synthetic enzyme preparations or in vivo using, for example, animal models in which abnormal destructive enzyme levels are found spontaneously (use of genetically mutate d or transgenic animals) or are induced by administration of exogenous agents or by surgery which disrupts joint stability.

Experimental

General Procedures

All reactions were performed in flame-dried or oven-dried glassware under a positive pressure of argon and were stirred magnetically unless otherwise indicated. Sensitive liquids and solutions were transferred via syringe or cannula and were introduced into reaction vessels through rubber septa. Reaction product solutions were concentrated using a Buchi evaporator unless otherwise indicated.

Materials

Commercial grade reagents and solvents were used without further purification except that diethyl ether and tetrahydrofuran were usually distilled under argon from benzophenone ketyl, and methylene chloride was distilled under argon from calcium hydride. Many of the specialty organic or organometallic starting materials and reagents were obtained from Aldrich, 1001 West Saint Paul Avenue, Milwaukee, Wis. 53233. Solvents are often obtained from EM Science as distributed by VWR Scientific.

Chromatography

Analytical thin-layer chromatography (TLC) was performed on Whatman® pre-coated glass-backed silica gel 60 A F-254 250 μm plates. Visualization of spots was effected by one of the following techniques: (a) ultraviolet illumination, (b) exposure to iodine vapor, (c) immersion of the plate in a 10% solution of phosphomolybdic acid in ethanol followed by heating, and (d) immersion of the plate in a 3% solution of p-anisaldehyde in ethanol containing 0.5% concentrated sulfuric acid followed by heating.

Column chromatography was performed using 230–400 mesh EM Science® silica gel.

Analytical high performance liquid chromatography (HPLC) was performed at 1 mL min$^{-1}$ on a 4.6×250 mm Microsorb® column monitored at 288 nm, and semi-preparative HPLC was performed at 24 mL min$^{-1}$ on a 21.4×250 mm Microsorb® column monitored at 288 nm.

Instrumentation

Melting points (mp) were determined with a Thomas-Hoover melting point apparatus and are uncorrected.

Proton ($^1$H) nuclear magnetic resonance (NMR) spectra (except for NOESY experiments) were measured with a General Electric GN-OMEGA 300 (300 MHz) spectrometer, and carbon thirteen ($^{13}$C) NMR spectra were measured with a General Electric GN-OMEGA 300 (75 MHz) spectrometer. Most of the compounds synthesized in the experiments below were analyzed by nmr, and the spectra were consistent with the proposed structures in each case.

The $^1$HNMR NOESY (Nuclear Overhauser Effect Spectroscopy) spectra were collected in-house on a Bruker DMX-500 ($^1$H=500.15 MHz, $^{13}$C=125.78 MHz) NMR spectrometer. Data processing was performed using the Bruker XWINNMR software on a Silicon Graphics Indy computer.

Mass spectral (MS) data were obtained on a Kratos Concept 1-H spectrometer by liquid-cesium secondary ion (LCIMS), an updated version of fast atom bombardment (FAB). Most of the compounds synthesized in the experiments below were analyzed by mass spectroscopy, and the spectra were consistent with the proposed structures in each case.

General Comments

For multi-step procedures, sequential steps are indicated by numbers. Variations within steps are indicated by letters. Dashed lines in tabular data indicates point of attachment.

Experimental Procedures

EXAMPLES 1 AND 2

Preparation of [2S, 4R]-4-[4-(4-chlorophenyl)phenyl]-4R-hydroxy-2-(phenylthiomethyl)butanoic acid and [2S, 4S]-4-[4-(4-chlorophenyl)phenyl]-4-hydroxy-2-(phenylthiomethyl)butanoic acid

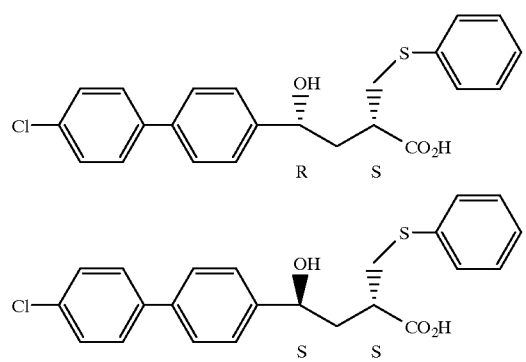

[S]-4-[4-(4-Chlorophenyl)phenyl]-4-oxo-2-(phenylthiomethyl)-butanoic acid (Reference Compound A) was prepared as described in WO-09615096 (Example 197).

A solution of this material (6.52 g, 15.9 mmol) in absolute ethanol (100 ml) was stirred under argon with ice bath (0° C.) cooling as sodium borohyride (4.12 g, 109 mmol) was added in portions. The reaction mixture was stirred as the ice bath melted and then at ambient temperature overnight. The resultant mixture which contained significant white solid was quenched by the addition of water (100 ml) and then evaporated in vacuo to ca. ⅓ volume. The condensed mixture was mixed with ca. 100 ml of ethyl acetate and then mixed vigorously as it was cautiously quenched with 1N hydrochloric acid until the aqueous phase was strongly acidic (evolution of hydrogen gas from excess borohydride). The aqueous phase was removed and the organic was washed several times with water, then brine and then dried over sodium sulfate and evaporated in vacuo. The residue was dissolved as much as possible in 100 ml of a methylene chloride/methanol mixture (99:1) and then filtered to remove a white solid which proved to be pure single isomer [2S, 4S]-4-[4-(4-chlorophenyl)phenyl]-4-hydroxy-2-(phenylthiomethyl)-butanoic acid as shown by analytical HPLC (silica column, 1 ml/min. 99:1 methylene chloride/methanol plus 0.05% acetic acid, peak detection at 254 nM, this 4-S isomer is the second to elute). The filtrate was chromatographed on a preparative (46 mm ID) silica HPLC column using the same solvent at 80 ml/min. to yield 444 mg of pure 4R isomer by condensation of the best fractions in vacuo to a low volume, cooling and collection of crystals by filtration.

Substantial material which eluted very early was found to be a mixture of the lactone isomers of the 4-hydroxy acids which were separated as shown in the procedures for reference compounds B and C. NMR evaluation of the lactones and correlation of those isomers with those of Examples 1 and 2 led to identification of the stereochemistry at carbon-4 of the hydroxy acids (see procedures for compounds B and C).

Example 1 (2S, 4R): MW 122–123° C.; HPLC (1 ml/min. 1% methanol in methylene chloride plus 0.05% acetic acid, Rainin 4.6 mm×25 cm silica column) 'R=10.02 min.; [α]$_D$+ 64.4 ° (c 0.55, acetone); $^1$HNMR (Acetone-d$_6$) δ7.12–7.7 (m, 13H), 4.82 (dd, J=4.04, 8.45 Hz, 1H), 3.2 (m, 2H), 2.98 (m, 1H), others under acetone peak.

Example 2 (2S, 4S): MP 137–138° C.; HPLC (conditions above) 'R =13.11 min.; [α]$_D$++28.8° c 0.93, acetone); $^1$HNMR (Acetone-d$_6$) δ7.15–7.7 (m, 13H), 4.83 (dd, J=5.88, 8.46 Hz, 1H), 3.25 (d, J=6.61 Hz, 2H), 2.79 (m, 1H), 1.95–2.25 (m, 2H).

Reference Compounds B and C

Isolation of [2S, 4R]-4-[4-(4-chlorophenyl)phenyl]-2-(phenylthiomethyl)-γ-butyrolactone and [2S,4S]-4-[4-(4-chlorophenyl)phenyl]-2-(phenylthio-methyl)-γ-butyrolactone

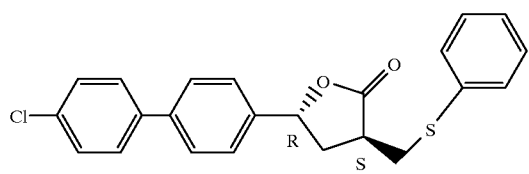

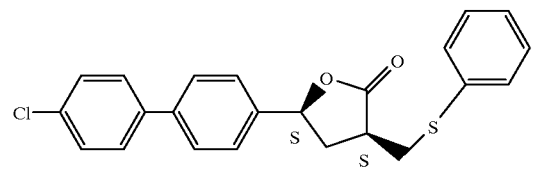

Preparative HPLC of the condensed early fractions from purification of [2S, 4S and R]-4-[4-(4-chlorophenyl)phenyl]-4-hydroxy-2-(phenylthiomethyl)-butanoic acid on silica columns using either 5% ethyl acetate in hexane or a slow gradient of 0–1% methanol in methylene chloride led to the isolation of pure samples of each of the γ-butyrolactone isomers (Reference compounds B and C).

Determination of the relative stereochemistry around chiral ring carbons can be achieved by identifying the relative position of the protons attached to these carbons, i.e. whether pairs of protons are on the same or on the opposite side of the ring plane. NMR spectroscopy, in particular one- or two-dimensional nuclear Overhauser spectroscopy (NOESY), is the ideal technique to solve this problem, taking advantage of differential nuclear Overhauser enhancements (NOEs) based on the relative spatial proximity of protons. See Macura, S. and Ernst, R. R., J. Mol. Biol., 1980, 206, 397. This was done for the two isomers of the γ-butyrolactone to show a greater NOE between H-1 and H-4 of the isomer with those protons cis (2S, 4S) than that of the isomer with those protons trans (2S, 4R). All other NOEs observed between the other protons on the lactone ring and attached CH$_2$ of the two isomers were self consistent with this interpretation.

While the purified crystalline hydroxy acids (Examples 1 and 2) are relatively stable as solids, aged solutions of these compounds slowly showed one or other of the lactones as a result of spontaneous lactonization occurring. This was evidenced by the chemical shift of H-4 on the 4S lactone at δ5.40 ppm and that on the 4R lactone at δ5.65 ppm. The hydroxy acid that converted to the 2S, 4R lactone was thus identified as the 2S, 4R hydroxy acid (Example 1) and that which converted to the 2S, 4S lactone was identified as the 2S, 4S hydroxy acid (Example 2).

Compound B (2S, 4R): MP 122–123° C.; $^1$HNMR (CDCl$_3$, 500 MHz) δ7.21–7.60 (series of m, 13H, aromatic H), 5.65 (dd, J=4.59, 7.98 Hz, 1H, H-4), 3.55 (dd, J=3.74, 13.29 Hz, 1H, SCH), 3.04 (dd, J=9.97, 13.28 Hz, 1H, SCH), 2.94–2.98 (m, 1H, H-2), 2.64–2.70 (m, 1H, H-3A), 2.46–2.51 (m, 1H, H-3B).

Compound C (2S, 4S): MP 142–143° C.; $^1$HNMR (CDCl$_3$, 500 MHz) δ7.21–7.60 (series of m, 13H, aromatic H), 5.40 (dd, J=5.79, 10.58 Hz, 1H, H-4), 3.65 (dd, J=3.50, 13.40 Hz, 1H, SCH), 2.96 (dd, J=9.90, 13.37 Hz, 1H, SCH), 3.02–3.07 (m, 1H, H-2), 2.87–2.92 (m, 1H, H-3A), 2.07 (dd, J=12.26,23.08 Hz, 1H, H-3B).

EXAMPLES 3 AND 4

Preparation of [2S, 4R]-4-[4-(4-chlorophenyl)phenyl]-4R-hydroxy-2-(3-phenylpropyl)butanoic acid and [2S, 4S]-4-[4-(4-chlorophenyl)-phenyl]-4-hydroxy-2-(3-phenylpropyl)butanoic acid:

17

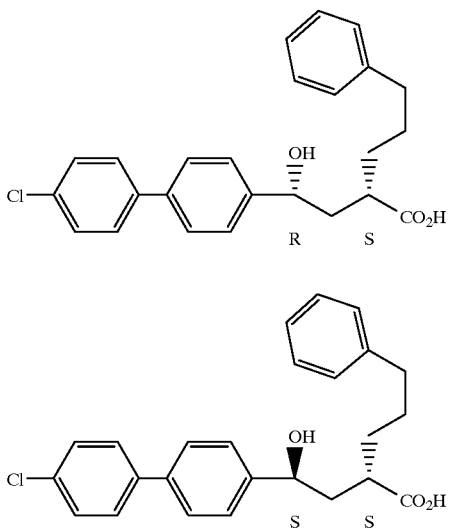

[S]-4-[4-(4-Chlorophenyl)phenyl]-4-oxo-2-(phenylpropyl)butanoic acid (Reference Compound D) was prepared as described in WO-09615096 (Example 116). A solution of this material (1.00 g, 2.46 mmol) in absolute ethanol (30 ml) was stirred under argon with ice bath (0° C.) cooling as sodium borohydride (0.743 g, 19.6 mmol) was added in portions. The reaction mixture was stirred as the ice bath melted and then at ambient temperature several days. The resultant mixture which contained significant white solid was quenched by the addition of water (150 ml) and ethyl acetate and the resultant mixture was stirred vigorously as concentrated sulfuric acid was added dropwise to make the aqueous phase strongly acidic. The aqueous phase was removed and the organic was washed several times with water, dried over sodium sulfate and evaporated in vacuo. The white residue was chromatographed on a preparative HPLC column (Prochrom packed with 13–23 μm angular silica) using 1% methanol in methylene chloride to yield 292 mg of pure first eluting isomer and 267 mg of pure second eluting isomer.

γ-Lactones can be formed from the 4-hydroxycarboxylic acid isomers by treatment of each separately with traces of toluenesulfonic acid in benzene at reflux using a Dean Stark trap to remove water. Nuclear Overhauser spectroscopy (NOESY) experiments on the lactones can then be used to establish which of these lactone isomers has the 4S and which the 4R stereochemistry and consequently which of the hydroxycarboxylic acids has each stereochemistry as conversion to lactone does not result in a change of stereochemistry.

Example 3 (or 4) (First eluting): MP 103–104° C.; HPLC (2 ml/min. 1% methanol in methylene chloride, Rainin 4.6 mm×15 cm silica column) 'R=6.55 min.; $^1$HNMR (DMSO-$d_6$) δ12.10 (s, 1H), 7.65 (d, J=8.46 Hz, 2H), 7.59 (d, J=8.46 Hz, 2H), 7.48 (d, J=8.46 Hz, 2H), 7.34 (d, J=8.09 Hz, 2H), 7.24 (t, J=7.36 Hz, 2H), 7.11–7.15 (m, 3H), 5.28 (d, J=4.78 Hz, 1H, OH), 4.46–4.52 (m, 1H), 2.46–2.61 (m, 3H partially under DMSO), 1.76–1.89 (m, 1H), 1.36–1.65 (m, 5H).

Example 4 (or 3) (Second eluting): MP 155–157° C.; HPLC (conditions above) 'R =9.75 min.; $^1$HNMR (DMSO-$d_6$) δ12.04 (s, 1H), 7.66 (d, J=8.82 Hz, 2H), 7.60 (d, J=8.46 Hz, 2H), 7.48 (d, J=8.46 Hz, 2H), 7.36 (d, J=8.09 Hz, 2H), 7.22 (t, J=6.99 Hz, 2H), 7.10–7.15 (m, 3H), 5.28 (bs, 1H, OH), 4.49 (bm, 1H), 2.3–2.7 (m, 2H under DMSO), 2.21–2.28 (m, 1H), 1.88–1.97 (m, 1H), 1.4–1.65 (m, 5H).

18

Reference Compounds F and G

Isolation of [2S]-4-[4-(4-chlorophenyl)phenyl]-4-oxo-2-[(4-hydroxy-phenyl)thiomethyl]butanoic acid and [2R]-4-[4-(4-chlorophenyl)phenyl]-4-oxo-2-[(4-hydroxyphenyl)thiomethyl]butanoic acid

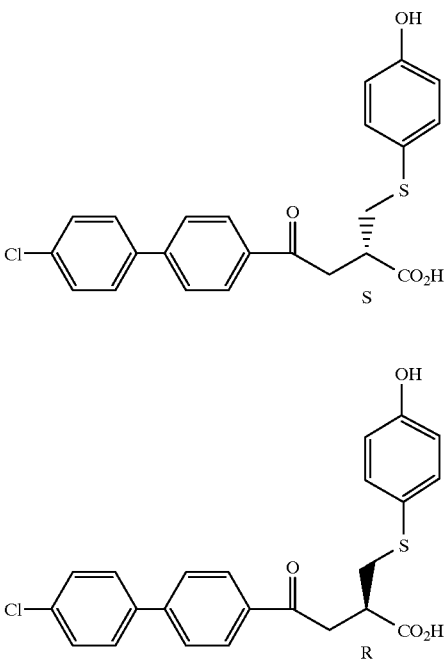

Racemic 4-[4-(4-chlorophenyl)phenyl]-4-oxo-2-[(4-hydroxyphenyl)-thio-methyl]butanoic acid (5.6 g) was prepared as described in WO-09615096 (Example 204). Chromatography of this material on a proprietary chiral stationary phase according to the general procedures of: D. Arlt, B. Boemer, R. Grosser and W. Lange, Angew. Chem. Int. Ed. Engl. 30 (1991) No. 12, pages 1662–1664 was used to separate this racemate into the enantiomers. The first isomer to elute was the 2S isomer (1.60 g) with a plus sign of rotation and the second to elute was the 2R isomer (1.43 g) with a negative sign of rotation.

Compound F (2S): MP 130–132° C.; HPLC (1 ml/min. 1% ethanol in hexane, Proprietary 4.6 mm×25 cm chiral column) 'R=7.72 min., 99.6% pure; $[\alpha]_D$+102.6° (c 0.88, Acetone); $^1$HNMR (CD$_3$OD) δ7.97 (d, J=8.46 Hz, 2H), 7.69 (d, J=8.46 Hz, 2H), 7.64 (d, J=8.45 Hz, 2H), 7.44 (d, J=8.82 Hz, 2H), 7.28 (d, J=8.46Hz, 2H), 6.70 (d, J=8.82Hz, 2H), 4.86 (bs, 2H), 2.98–3.54 (series of m, 5H).

Compound G (2R): HPLC (1 ml/min. 1% ethanol in hexane, Proprietary 4.6 mm×25 cm chiral column) 'R=10.80 min., 99.8% pure; $[\alpha]_D$–103.8° (c 1.0, Acetone); $^1$HNMR (CD$_3$OD) Same as Compound C.

EXAMPLES 5 AND 6

Preparation of [2S, 4R]-4-[4-(4-chlorophenyl)phenyl]-4-hydroxy-2-[(4-hydroxyphenyl)thiomethyl]butanoic acid and [2S, 4S]-4-[4-(4-chlorophenyl)-phenyl]-4-hydroxy-2-[(4hydroxyphenyl)thiomethyl]butanoic acid:

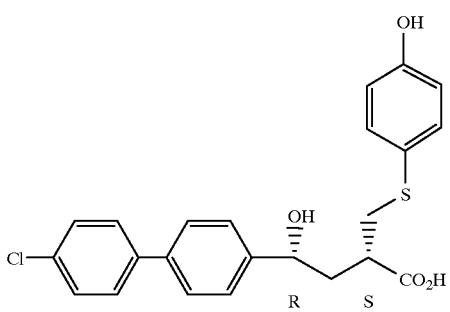

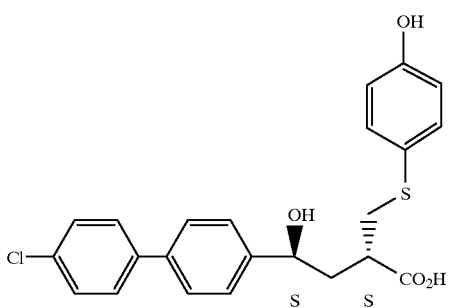

The general method of Examples 1 and 2 can be used to prepare these compounds except that the above Reference Compound F is used rather than [S]-4-[4-(4-Chlorophenyl)phenyl]-4-oxo-2-(phenylthiomethyl)butanoic acid.

EXAMPLES 7–16

The names and structures are shown below. The general method of Examples 5 and 6 can be used to prepare the compounds of Examples 9–20 except that the appropriate 4-oxo compounds as prepared according to the procedures of WO-09615096 are used rather than [S]-4-[4-(4-Chlorophenyl)phenyl]-4-oxo-2-(2-phthalimidoethyl)butanoic acid.

| Compound from WO-09615096 | Used to make |
|---|---|
| 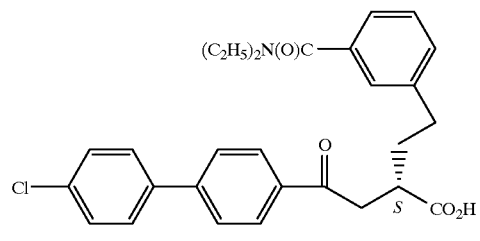<br>Example | Examples 7 and 8 |
| 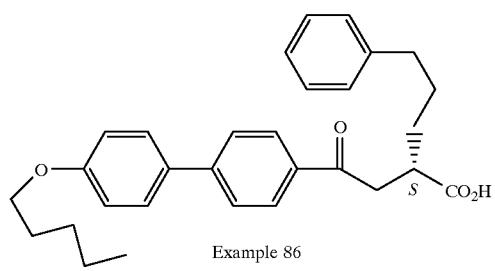<br>Example 86 | Examples 9 and 10 |
| 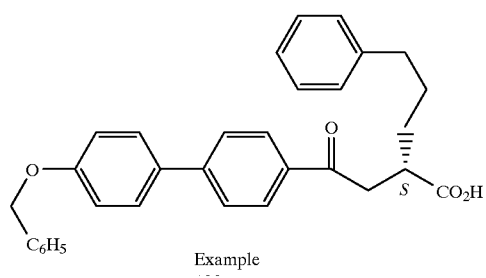<br>Example | Examples 11 and 12 |

EXAMPLES 7–8

Preparation of [2S, 4R]-4-[4-(4-chlorophenyl)phenyl]-4-hydroxy-2-[2-(3-N,N-diethylcarbamoyl)phenylethyl]butanoic acid and [2S, 4S]-4-[4-(4-chlorophenyl)phenyl]-4-hydroxy-2-[2-(3-NN-diethylcarbamoyl)-phenylethyl]-butanoic acid

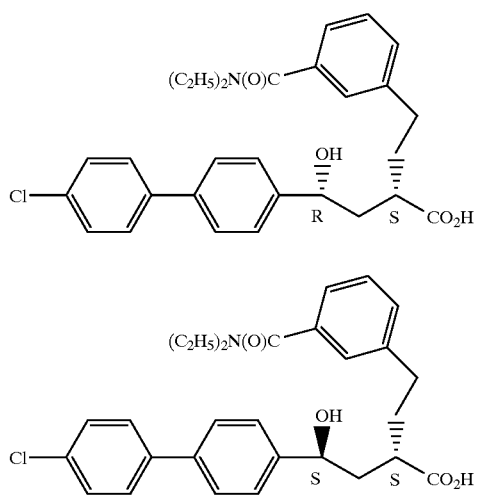

EXAMPLES 9–10

Preparation of [2S, 4R]-4-[4-(4-pentyloxyphenyl)phenyl]-4-hydroxy-2-(3-phenylpropyl)butanoic acid; [2S, 4S]-4-[4-(4-pentyloxyphenyl)phenyl]-4-hydroxy-2-(3-phenylpropyl)butanoic acid

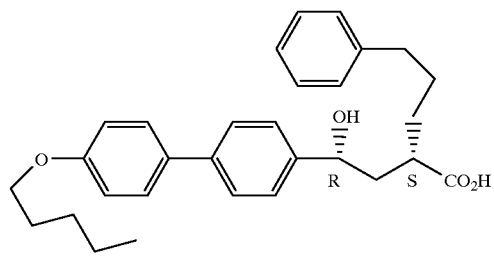

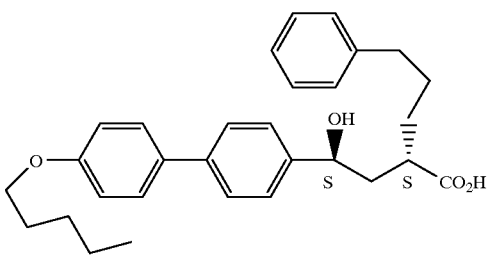

EXAMPLES 11–12

Preparation of [2S, 4R]-4-[4-(4-benzyloxyphenyl)-phenyl]-4-hydroxy-2-(3-phenylpropyl)butanoic acid and [2S, 4S]-4-[4-(4-benzyloxy-phenyl)-phenyl]-4-hydroxy-2-(3-phenylpropyl)butanoic acid

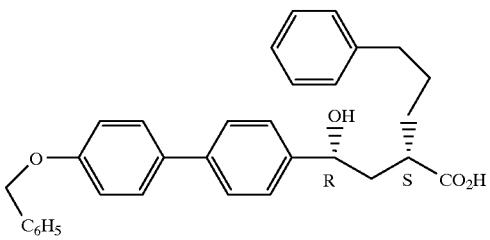

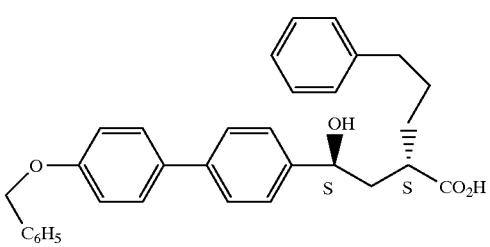

EXAMPLES 13–14

Preparation of (1S,2R,5S)-trans-5-[(4-(4-chlorophenyl)-phenyl)-S-hydroxymethyl]-trans-2-phenylthiocyclopentanecarboxylic acid and (1S,2R,5S)-trans-5-[(4-(4-chlorophenyl)phenyl)-R-hydroxymethyl]-trans-2-phenylthiocyclopentanecarboxylic acid

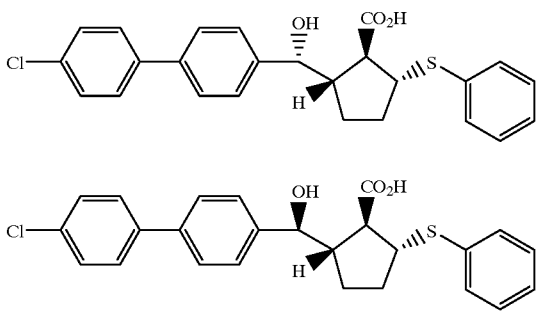

EXAMPLES 15–16

Preparation of (1S,2S,5S)-trans-5-[(4-(4-chlorophenyl)-phenyl)-S-hydroxymethyl]-cis-2-(2-methoxycarbonylphenylthio)-cyclopentane-carboxylic acid and (1S,2S,5S)-trans-5-[(4-(4-chlorophenyl)-phenyl)-R-hydroxymethyl]-cis-2-(2-methoxycarbonylphenylthio)cyclo-pentane-carboxylic acid

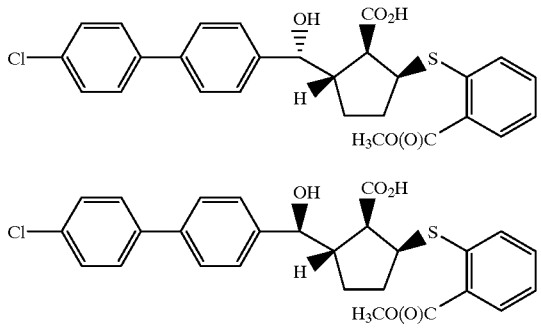

Biological Protocols and in vitro Test Data

P218 Quenched Fluorescence Assay for MMP Inhibition

The P218 quenched fluorescence assay (Microfluorometric Profiling Assay) is a modification of that originally described by C. G. Knight et al., FEBS Letters, 296, 263–266 (1992) for a related substrate and a variety of matrix metalloproteinases (MMPs) in cuvettes. The assay was run with each exemplary compound of the invention and the three MMPs, MMP-3, MMP-9 and MMP-2, analyzed in parallel, adapted as follows for a 96-well microtitre plate and a Hamilton AT® workstation.

P218 Fluorogenic Substrate

P218 is a synthetic substrate containing a 4-acetyl-7-methoxycoumarin (MCA) group in the N-terminal position and a 3-(2,4-dinitrophenyl)-(L)-2,3-diaminopropionyl (DPA) group internally. This is a modification of a peptide reported by Knight (1992) that was used as a substrate for matrix metalloproteinases. Once the P218 peptide is cleaved (putative clip site at the Ala-Leu bond), the fluorescence of the MCA group can be detected on a fluorometer with excitation at 328 nm and emission at 393 nm. P218 is currently being produced by BACHEM Bioscience, Inc. exclusively for the Bayer Corp. P218 has the structure:

H-MCA-Pro-Lys-Pro-Leu-Ala-Leu-DPA-Ala-Arg-NH$_2$ (MW 1332.2)

Recombinant Human CHO Stromelysin (MMP-3)

Recombinant Human CHO Pro-MMP-3: Human CHO pro-stromelysin-257 (pro-MMP-3) was expressed and purified as described by T. J. Housley et al., J. Biol. Chem., 268, 4481–4487 (1993).

Activation of Pro-MMP-3: Pro-MMP-3 at 1.72 $\mu$M (100 $\mu$g/mL) in an MMP-3 activation buffer consisting of 5 mM Tris at pH 7.5, 5 mM CaCl$_2$, 25 mM NaCl, and 0.005% Brij-35 was activated by incubation with TPCK (N-tosyl-(L)-phenylalanine chloromethyl ketone) trypsin (1:100 w/w to pro-MMP-3) at 25° C. for 30 min. The reaction was stopped by addition of soybean trypsin inhibitor (SBTI; 5:1 w/w to trypsin concentration). This activation protocol results in formation of 45 kDa active MMP-3, which still contains the C-terminal portion of the enzyme.

Preparation of Human Recombinant Pro-gelatinase A (MMP-2)

Human Recombinant Pro-MMP-2: Human pro-gelatinase A (pro-MMP-2) was prepared using a vaccinia expression system according to the method of R. Fridman et al., J. Biol. Chem., 15398–405, (1992).

Activation of Pro-MMP-2: Pro-MMP-2 at 252 mg/mL was diluted 1:5 to a final concentration of 50 mg/mL solution in an MMP-2 activation buffer consisting of 25 mM Tris at pH 7.5, 5 mM CaCl$_2$, 150 mM NaCl, and 0.005% Brij-35. p-Aminophenylmercuric acetate (APMA) was prepared at 10 mM (3.5 mg/mL) in 0.05 N NaOH. The APMA solution was added at 1/20 the reaction volume for a final APMA concentration of 0.5 mM, and the enzyme was incubated at 37° C. for 30 min. Activated MMP-2 (15 mL) was dialyzed twice vs. 2 L of MMP-2 activation buffer (dialysis membranes were pretreated with a solution consisting of 0.1% BSA in MMP-2 activation buffer for 1 min., followed by extensive H$_2$O washing). The enzyme was concentrated on Centricon concentrators (concentrators were also pretreated with a solution consisting of 0.1% BSA solution in MMP-2 activation buffer for 1 min., followed by washing with H$_2$O, then MMP-2 activation buffer) with redilution followed by reconcentration repeated twice. The enzyme was diluted to 7.5 mL (0.5 times the original volume) with MMP-2 activation buffer.

Preparation of Human Recombinant Pro-gelatinase B (MMP-9)

Human Recombinant Pro-MMP-9: Human recombinant pro-gelatinase B (pro-MMP-9) derived from U937 cDNA as described by S. M. Wilhelm et al., J. Biol. Chem., 264 17213–17221 (1989) was expressed as the full-length form using a baculovirus protein expression system. The pro-enzyme was purified using methods previously described by M. S. Hibbs, et al., J. Biol. Chem., 260, 2493–500 (1984).

Activation of Pro-MMP-9: Pro-MMP-9 (20 $\mu$g/mL) in an MMP-9 activation buffer consisting of 50 mM Tris at pH 7.4, 150 mM NaCl, 10 mM CaCl$_2$ and 0.005% Brij-35 was activated by incubation with a 0.5 mM p-aminophenylmercuric acetate (APMA) for 3.5 h at 37° C. The enzyme was dialyzed against the same buffer to remove APMA.

Instrumentation

Hamilton Microlab AT Plus®: The MMP-profiling assay was performed robotically using a Hamilton MicroLab AT Plus®. The Hamilton was programmed to: (1) serially dilute up to 11 potential inhibitors automatically using a 2.5 mM stock solution of the inhibitor in 100% DMSO; (2) distribute substrate followed by inhibitor into a 96well Cytofluor plate; and (3) add a single enzyme to the plate with mixing to start the reaction. Subsequent plates for each additional enzyme were prepared automatically by beginning the program at the substrate addition point, remixing the diluted inhibitors, and beginning the reaction by addition of enzyme. In this way, all MMP assays were done using the same inhibitor dilutions.

Millipore Cytofluor II: Following incubation, the plate was read on a Cytofluor II fluorometric plate reader with excitation at 340 nM and emission at 395 nM with the gain set at 80.

Buffers

*Microfluorometric Reaction Buffer* (MRB): Dilutions of test compounds, enzymes and P218 substrate for the microfluorometric assay were made in microfluorometric reaction buffer (MRB) consisting of 50 mM 2-(N-morpholino) ethanesulfonic acid (MES) at pH 6.5 with 10 mM $CaCl_2$, 150 mM NaCl, 0.005% Brij-35 and 1% DMSO.

Methods

*MMP Microfluorometric Profiling Assay.* The assay was done with a final P218 concentration of 6 μM, approximately 0.5 to 0.8 nM of activated MMP (one MMP per 96-well plate), and with variable inhibitor concentrations. The Hamilton MicroLab AT Plus® was programmed to serially dilute up to 11 compounds from a 2.5 mM stock (100% DMSO) to 10-times the final compound concentrations in the assay. Initially, the instrument delivered various amounts of microfluorometric reaction buffer (MRB) to a 96-tube rack of 1 mL Marsh dilution tubes. The instrument picked up 20 μL inhibitor (2.5 mM) and mixed it with buffer in row A of the Marsh rack, resulting in a 50 μM inhibitor concentration. The inhibitors were then serially diluted to 10, 5, 1, 0.2, 0.05 and 0.01 μM. Position 1 on the sample rack contained only DMSO for the "enzyme-only" wells in the assay, which resulted in no inhibitor in column 1, rows A through H. The instrument then distributed 107 μL of P218 to a single 96-well Cytofluor microtiter plate. The instrument re-mixed and loaded 14.5 μL of diluted compound from rows A to G in the Marsh rack to the corresponding rows in the microtiter plate. (Row H represented the "background" row. To this was added 39.5 μL of microfluorometric reaction buffer in place of drug or enzyme.) The reaction was started by adding 25 μL of the appropriate enzyme (at 5.86-times the final enzyme concentration) from a BSA-treated reagent reservoir to each well, excluding the Row H, the "background" row. (The enzyme reservoir was pre-treated with 1% BSA in 50 mM Tris at pH 7.5 containing 150 mM NaCl for 1 h at room temperature, followed by extensive washing with $H_2O$, and drying at room temp.)

After addition and mixing of the enzyme, the plate was covered and incubated for 25 min. at 37° C. Additional enzymes were tested in the same manner by beginning the Hamilton program with the distribution of P218 substrate to the microtiter plate, followed by re-mixing and distribution of the drug from the same Marsh rack to the microtiter plate. The second (or third, etc.) MMP to be tested was then distributed from a reagent rack to the microtiter plate with mixing, prior to covering and incubation.

*$IC_{50}$ Determination in Microfluorometric Assay:* Data generated on the Cytofluor II was copied from an exported ".CSV" file to a master Excel spreadsheet. Data from several different MMPs (one 96-well plate per MMP) were calculated simultaneously. The percent inhibition was determined for each drug concentration by comparing the amount of hydrolysis (fluorescence units generated over 25 minutes of hydrolysis) of wells containing compound with the "enzyme only" wells in column 1. Following subtraction of background, the percent inhibition was calculated as:

((Control values—Treated Values)/Control Values)×100

Percent inhibitions were determined for inhibitor concentrations of 5, 1, 0.5, 0.1, 0.02, 0.005 and 0.001 μM. Linear regression analysis of percent inhibition versus log inhibitor concentration was used to obtain $IC_{50}$ values.

Profiling Assay Data for Certain Compounds of the Invention

Table 5

MMP-Profiling Data. All $IC_{50}$ values are expressed as nM.

TABLE 5

MMP-Profiling Data. All $IC_{50}$ values are expressed as nM.

| Ex. # or Control Compound | MMP-3 $IC_{50}$ | MMP-9 $IC_{50}$ | MMP-2 $IC_{50}$ |
|---|---|---|---|
| 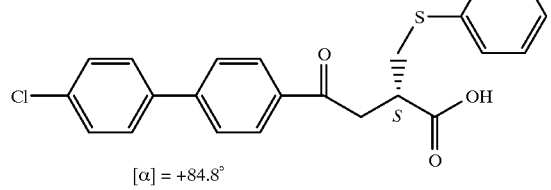 [α] = +84.8° | 193 | 492 | 20 |
| 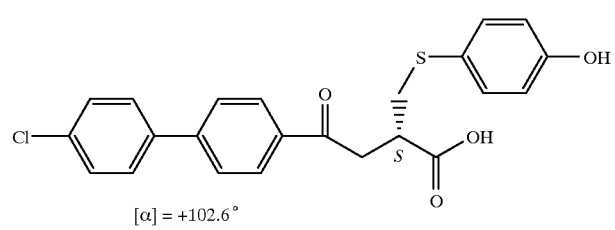 [α] = +102.6° | 155 | 115 | 3.0 |

TABLE 5-continued

MMP-Profiling Data. All IC$_{50}$ values are expressed as nM.

| Ex. # or Control Compound | MMP-3 IC$_{50}$ | MMP-9 IC$_{50}$ | MMP-2 IC$_{50}$ |
|---|---|---|---|
| [Structure: 4'-chlorobiphenyl-CH(OH,R)-CH$_2$-CH(S,CH$_2$-S-Ph)-COOH; [α] = +64.4°] | 34 | 58 | 2.8 |
| [Structure: 4'-chlorobiphenyl-CH(OH,S)-CH$_2$-CH(S,CH$_2$-S-Ph)-COOH; [α] = +28.8°] | 1,550 | 890 | 62 |
| [Structure: 4'-chlorobiphenyl-C(O)-CH$_2$-CH(S,CH$_2$CH$_2$-Ph)-COOH; [α] = +25.6°] | 108 | 209 | 34 |
| [Structure: 4'-chlorobiphenyl-CH(OH)-CH$_2$-CH(S,CH$_2$CH$_2$-Ph)-COOH; first eluting] | 50 | 82 | 9.4 |
| [Structure: 4'-chlorobiphenyl-C(O)-CH$_2$-CH(S,CH$_2$CH$_2$-Ph)-COOH; second eluting] | 1200 | 369 | 46 |

*The example numbers of diastereomers 3 and 4 may be reversed, as the stereochemistry at the carbon atom bearing the hydroxyl group has not been determined.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

We claim:

1. A compound having matrix metalloprotease inhibitory activity and the formula

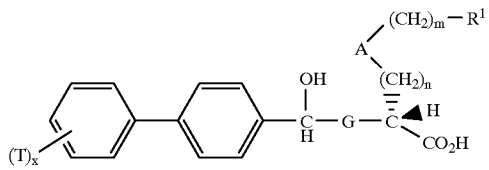

wherein:
T is a pharmaceutically-acceptable substituent group;
x is 0, 1, or 2;
m is 0 or an integer of 1–4;
n is 0 or 1; and
either
    A and G are both $CH_2$; or
    A is a chemical bond and G is $CH_2$; or
    A is CH or N; and
    G is CH; and
    A is connected to G by a ring-forming linkage of formula:
    $(CH_2)_{0-3}(Q)(CH_2)_{0-3}$; wherein
Q is a chemical bond, S, or O; and
C, S, and O constitute linking atoms;
    resulting in formation of a ring which includes A, said ring-forming linkage, and G;
    with the provisos that
        the sum of n plus the total number of linking atoms in said ring-forming linkage is an integer of from 1 to 4; and
        the number of heteroatoms in said ring is 0 or 1;
$R^1$ is:
    aryl of 6–10 carbons, provided that if this aryl group is phenyl, then x is 1 or 2;
    heteroaryl containing 4–9 carbons and at least one N, O or S heteroatom;
    aryl-substituted alkenyl wherein the aryl portion contains 6–10 carbons and the alkenyl portion contains 2–5 carbons;
    hetaryl-substituted alkenyl wherein the heteroaryl portion contains 4–9 carbons and at least one N, O, or S heteroatom, and the alkenyl portion contains 2–5 carbons;
    aryl-substituted alkynyl wherein the aryl portion contains 6–10 carbons and the alkynyl portion contains 2–5 carbons;
    heteroaryl-substituted alkynyl wherein the heteroaryl portion contains 4–9 carbons and at least one N, O, or S heteroarom and the alkynyl portion contains 2–5 carbons;
    N-phthalimidoyl;
    N-(1,2-naphthalenedicarboximidoyl);
    N-(2,3-naphthalenedicarboximidoyl);
    N-(1,8-naphthalenedicarboximidoyl);
    N-indoloyl;
    N-(2-pyrrolodinonyl);
    N-succinimidoyl;
    N-maleimidoyl;
    3-hydantoinyl;
    1,2,4-urazolyl;
    amido;
    a urethane;
    a urea;

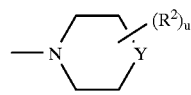

wherein Y is O or S, $R^2$ is H or alkyl of 1–3 carbon atoms, and u is 0, 1, or 2;
    an amino; and
    $ZR^8$ in which
        Z represents

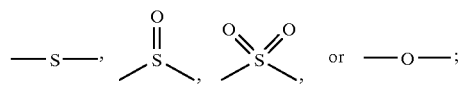

and
    $R^8$ is:
        aryl of 6–10 carbons;
        heteroaryl containing 4–9 carbons and at least one N, O, or S heteroatom;
        arylalkyl wherein the aryl portion contains 6–12 carbons and the alkyl portion contains 14 carbons; or
        heteroaryl-alkyl wherein the aryl portion contains 4–9 carbons and at least one N, O, or S heteroatom and the alkyl portion contains 1–4 carbons; or
and with the proviso that
    when Z is O, $R^8$ may also be alkyleneoxy or polyalkyleneoxy terminated with H, alkyl, or phenyl;
    aryl or heteroaryl portions of any of the T or $R^1$ groups optionally bearing up to two substituents selected from the group consisting of $-(CH_2)_yC(R^{11})(R^{12})OH$, $-(CH_2)_yOR^{11}$, $-(CH_2)_ySR^{11}$, $-(CH_2)_yS(O)R^{11}$, $-(CH_2)_yS(O)_2R^{11}$, $-(CH_2)_ySO_2N(R^{11})_2$, $-(CH_2)_yN(R^{11})_2$, $-(CH_2)_yN(R^{11})COR^{12}$, $-OC(R^{11})_2O-$ in which both oxygen atoms are connected to the aryl ring, $-(CH_2)_yCOR^{11}$, $-(CH_2)_yCON(R^{11})_2$, $-(CH_2)_yCO_2R^{11}$, $-(CH_2)_yOCOR^{11}$, -halogen, $-CHO$, $-CF_3$, $-NO_2$, $-CN$, and $-R^{12}$, in which y is 0–4; $R^{11}$ represents H or lower alkyl of 1–4 carbon atoms; and $R^{12}$ represents lower alkyl of 1–4 carbon atoms;
said compound being a mixture of diastereomers, or the single diastereomer which has the greater matrix metalloprotease inhibitory activity of the diastereomers constituting said mixture of diastereomers;
or a pharmaceutically-acceptable salt thereof.

2. The compound of claim 1 wherein
A is $CH_2$;
G is $CH_2$; and
n is O;
    said compound having the formula

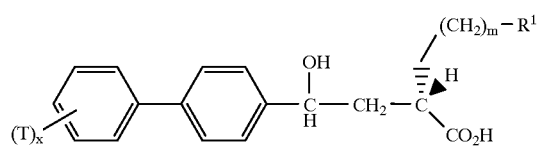

wherein

T, x, m, and $R^1$ are as defined in claim 1.

3. The compound of claim 2 wherein m is 0, 1, or 2; and when m is 0, $R^1$ is

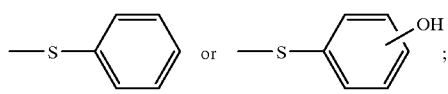

when m is 1, $R^1$ is

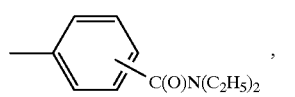

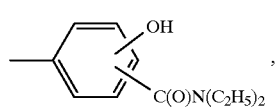

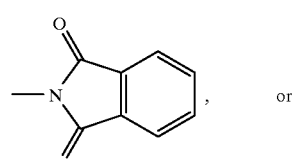

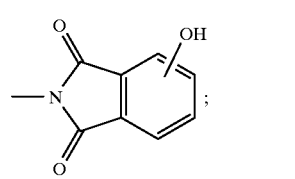

when m is 2, $R^1$ is

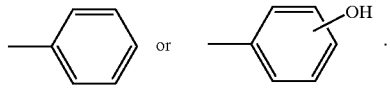

4. The compound of claim 3 wherein

T is halogen or $OR^6$ wherein $R^6$ is alkyl of 1–6 carbons or benzyl;

x is 1;

m is 0 or 2;

when m is 0, $R^1$ is

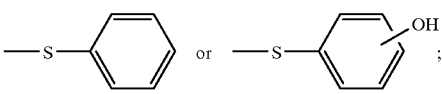

and when m is 2, $R^1$ is

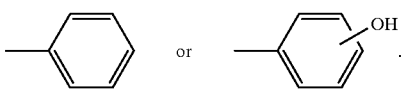

5. A compound of claim 2 having the name

4-[4-(4-chlorophenyl)phenyl]-4-hydroxy-2-(phenylthiomethyl)butanoic acid;

[2S, 4R]-4-[4-(4-chlorophenyl)phenyl]-4-hydroxy-2-(phenylthiomethyl)-butanoic acid;

4-[4-(4-chlorophenyl)phenyl]-4-hydroxy-2-[(4-hydroxyphenyl)-thiomethyl]-butanoic acid;

4-[4-(4-chlorophenyl)phenyl]-4-hydroxy-2-(3-phenylpropyl)butanoic acid;

4-[4-(4-chlorophenyl)phenyl]-4-hydroxy-2-[2-(3-N,N-diethylcarbamoyl)-phenylethyl]butanoic acid;

4-[4-(4-pentyloxyphenyl)phenyl]-4-hydroxy-2-(3-phenylpropyl)butanoic acid;

4-[4-(4-benzyloxyphenyl)phenyl]-4-hydroxy-2-(3-phenylpropyl)butanoic acid;

4-[4-(4-chlorophenyl)phenyl]-4-hydroxy-2-(2-phthalimidoethyl)butanoic acid.

6. The compound of claim 1 wherein n is 0 or 1; and

A is CH or N; and

G is CH; and

A is connected to G by a ring-forming linkage of formula:

$(CH_2)_{0-3}(Q)(CH_2)_{0-3}$; wherein

Q is a chemical bond, S, or O; and

C, S, and O constitute linking atoms;

resulting in formation of a ring which includes A, said ring-forming linkage, and G;

said compound having the formula

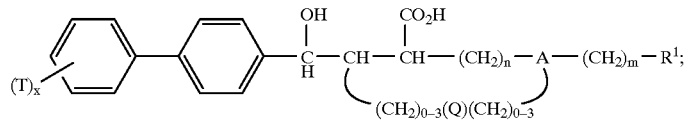

with the provisos that the sum of n plus the total number of linking atoms in said ring-forming linkage is an integer of from 1 to 4; and the number of heteroatoms in said ring is 0 or 1;

T, x, m, and $R^1$ being as defined in claim 1.

7. The compound of claim 6 wherein n is 0;

A is CH;

Q is a chemical bond; and said ring-forming linkage is —$(CH_2)_2$—; and said compound having the formula

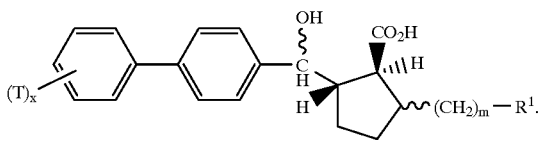

8. The compound of claim 7 wherein
   T is halogen or $OR^6$ wherein $R^6$ is alkyl of 1–6 carbons or benzyl;
   x is 1;
   m is 0 or 1; and
   when m is 0, $R^1$ is

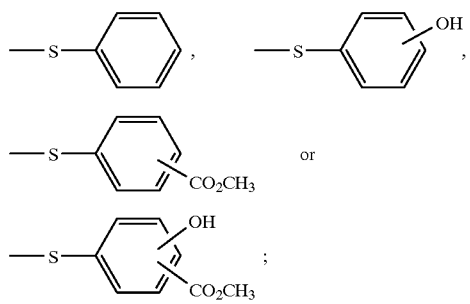

when m is 1, $R^1$ is

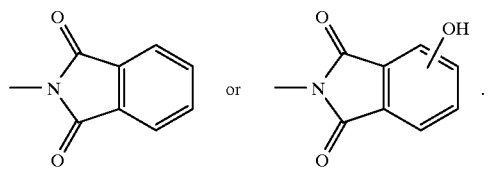

9. A compound of claim 6, having the name
   trans-5-[(4-(4-chlorophenyl)phenyl)hydroxymethyl]-trans-2-phenylthio-cyclopentanecarboxylic acid;
   trans-5-[(4-(4-chlorophenyl)phenyl)hydroxymethyl]-cis-2-(2-methoxycarbonyl-phenylthio)cyclopentanecarboxylic acid; and
   trans-5-[(4-(4-chlorophenyl)phenyl)hydroxymethyl]-trans-2-phthalimidomethylcyclopentanecarboxylic acid.

10. A pharmaceutical composition comprising a compound of claim 1 and a pharmaceutically acceptable carrier.

11. A pharmaceutical composition comprising a compound of claim 2 and a pharmaceutically acceptable carrier.

12. A pharmaceutical composition comprising a compound of claim 6 and a pharmaceutically acceptable carrier.

13. A method for treating a matrix metalloprotease-mediated condition in a mammal comprising administering to said mammal an amount of a compound of claim 1 which is effective to treat said condition.

14. The method of claim 13 wherein said mammal is a human.

15. The method of claim 13 wherein the effect the treatment of is: alleviation of osteoarthritis, rheumatoid arthritis, septic arthritis, periodontal disease, corneal ulceration, proteinuria, aneurysmal aortic disease, dystrophobic epidermolysis bullosa, conditions leading to inflammatory responses, osteopenias mediated by MMP activity, tempero mandibular joint disease, or demyelating diseases of the nervous system; retardation of tumor metastasis or degenerative cartilage loss following traumatic joint injury; reduction of coronary thrombosis from atherosclerotic plaque rupture; or improved birth control; and said amount of a compound of claim 1 is effective to inhibit the activity of at least one matrix metalloprotease in said mammal, thereby to achieve said effect.

16. A method of preparing a compound of formula

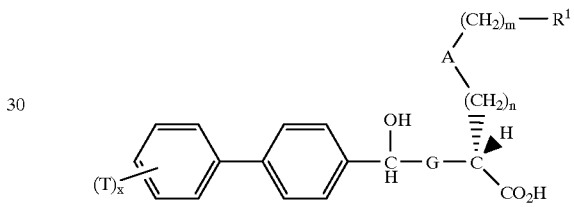

comprising:
   reducing to a hydroxyl group the ketone carbonyl in a compound of formula

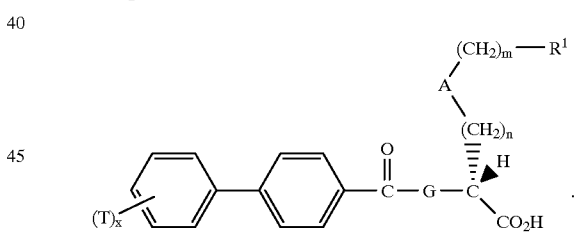

wherein T, x, G, n, A, m, and $R^1$ are as defined in claim 1.

* * * * *